(12) United States Patent
Li et al.

(10) Patent No.: US 11,399,782 B2
(45) Date of Patent: Aug. 2, 2022

(54) MEDICAL RADIATION PROTECTION DEVICE

(71) Applicant: Chunjian Li, Nanjing (CN)

(72) Inventors: Chunjian Li, Nanjing (CN); Yule Li, Nanjing (CN)

(73) Assignee: Chunjian Li, Nanjing (CN)

( * ) Notice: Subject to any disclaimer, the term of this patent is extended or adjusted under 35 U.S.C. 154(b) by 0 days.

(21) Appl. No.: 16/976,966

(22) PCT Filed: Dec. 10, 2018

(86) PCT No.: PCT/CN2018/120143
§ 371 (c)(1),
(2) Date: Aug. 31, 2020

(87) PCT Pub. No.: WO2020/015282
PCT Pub. Date: Jan. 23, 2020

(65) Prior Publication Data
US 2021/0128085 A1    May 6, 2021

(30) Foreign Application Priority Data

Jul. 19, 2018    (CN) .......................... 201810798742.1
Jul. 19, 2018    (CN) .......................... 201821148220.9

(51) Int. Cl.
*A61B 6/10*    (2006.01)
*A61B 6/00*    (2006.01)

(52) U.S. Cl.
CPC ............ *A61B 6/107* (2013.01); *A61B 6/4405* (2013.01)

(58) Field of Classification Search
CPC ............................. A61B 6/107; A61B 6/4405
See application file for complete search history.

(56) References Cited

U.S. PATENT DOCUMENTS

2008/0093568 A1    4/2008    Fox et al.
2011/0253914 A1    10/2011    Rees

FOREIGN PATENT DOCUMENTS

| CN | 203122453 U | 8/2013 |
| CN | 204049675 U | 12/2014 |
| CN | 105007823 A | 10/2015 |
| CN | 107498159 A | 12/2017 |

OTHER PUBLICATIONS

International Search Report of PCT/CN2018/120143.
Written Opinion of PCT/CN2018/120143.

*Primary Examiner* — Nicole M Ippolito
*Assistant Examiner* — Hanway Chang
(74) *Attorney, Agent, or Firm* — Dragon Sun Law Firm, PC; Jinggao Li, Esq.; Nathaniel Perkins

(57) ABSTRACT

The present disclosure relates to a medical radiation protection device, which comprises a barrel-shaped protecting frame and a protecting cover. The barrel-shaped protecting frame comprises an upper protecting frame and a lower protecting frame. The upper protecting frame is connected to the lower protecting frame, and the upper protecting frame may move up or down along the lower protecting frame. The protecting cover is arranged on the side wall of the barrel-shaped protecting frame. The medical radiation protection device of the present disclosure can realize non-wearable X-ray protection, reduce load of the surgeon doctor and improve effectiveness of protection therefor. The protection device is operable via a universal caster, does not get in the way of operation of the surgeon doctor, and is thus convenient for maneuvering of the surgeon doctor.

13 Claims, 15 Drawing Sheets

MEDICAL RADIATION PROTECTION DEVICE

CROSS REFERENCE TO RELATED APPLICATIONS

This application is the national phase entry of International Application No. PCT/CN2018/120143, filed on Dec. 10, 2018, which claims priority to Chinese application CN201821148220.9, filed on Jul. 19, 2018, and CN201810798742.1, filed on Jul. 19, 2018, the entire contents of which are incorporated herein by reference.

TECHNICAL FIELD

The disclosure relates to the field of medical radiation protection, and in particular relates to an X-ray protection device for interventional treatment.

BACKGROUND

Medical radioactive sources and radiation devices have been widely used in clinical medicine, which greatly improves the diagnosis and treatment of diseases. However, radiation generated by radioactive sources and radiation devices is harmful to human health, with improper use or improper protection liable to result in radiation accidents. Strengthening the safety of radiation protection in hospitals is of paramount importance for the protection of medical workers.

Interventional therapy is a discipline that has emerged on the basis of diagnostic imaging. Its development has greatly improved the diagnosis and treatment of diseases. However, most interventional diagnostics and treatments need to be performed under the guidance of X-ray fluoroscopy and angiography. Interventional treatment operators who work under X-rays for a long time will undoubtedly suffer radiation damage. Therefore, interventional operators must take strict protective measures when performing an interventional operation.

At present, an interventional protection device is mainly made of lead, including lead clothing, lead caps, lead masks, lead collars and so on. Such like protection devices albeit meet the requirements for radiation protection, doctors wearing heavy lead clothing have difficulty in performing operation in standing position for long periods of time (such as complex lesions or multiple consecutive operations) due to the heavy weight of lead materials. Many interventional doctors suffer chronic damage due to long-term high load on their bodies. Relatively thinner and lighter lead clothing has begun to appear on the market, but doctors still have to bear a heavy weight, while thin lead clothing might result in reduced radiation protection.

SUMMARY OF THE INVENTION

The technical problem to be solved by the present disclosure is to provide a medical radiation protection device, which solves the problem of long-time weight bearing for a surgeon doctor and poor protective effect of lead protective clothing that the surgeon doctor performing an interventional operation has to wear.

In order to solve the above technical problem, the present disclosure provides a floor-standing medical radiation protection device comprising a barrel-shaped protecting frame and a protecting cover, the barrel-shaped protecting frame comprising an upper protecting frame and a lower protecting frame. Further, the medical radiation protection device further comprises a lifting system, and the lifting system comprises a lifting motor, a lifting mechanism, and a lifting control device. The upper protecting frame is connected to the lower protecting frame via the lifting mechanism. The upper protecting frame is supported by the lower protecting frame to move up or down along the lower protecting frame under action of the lifting mechanism. The protecting cover is arranged on a side wall of the barrel-shaped protecting frame.

The lifting control device comprises a button switch, a voice control device, or a gesture control device.

Further, the upper protecting frame comprises an upper protecting frame console and at least a first support rod, and the upper protecting frame console comprises an upper protecting frame console panel and an upper protecting frame console support frame, and the upper protecting frame console panel is fixed on the upper protecting frame console support frame via a screw;

The first support rod is fixedly connected to a lower bottom surface of the upper protecting frame console and to the lifting mechanism and is under control of the lifting mechanism for up or down movement; The lower protecting frame comprises a middle protecting frame support, a bottom support and a second support rod, with the middle protecting frame support and the bottom support being fixedly connected via the second support rod.

The lifting mechanism and the lifting motor are fixed on the middle protecting frame support.

The upper protecting frame console, the middle protecting frame support and the bottom support have a same cross-sectional shape. The upper protecting frame console is provided with a door panel along a secant direction, and a front and a rear side each of the door panel is in planar shape; correspondingly, the middle protecting frame support and the bottom support each is respectively provided with a door panel along a respective secant direction, and a front and a rear side each of the door plate is in planar shape.

The medical radiation protection device further comprises a charging device, with the charging device comprising a charging interface, a rechargeable battery and a power transmission interface, and the charging device is mounted on the lower protecting frame; the lifting motor is electrically connected to the power transmission interface.

The medical radiation protection device further comprises a power switch and a power indicator device, the power switch and the power indicator device being mounted on the upper protecting frame console. The power switch and the power indicator device are electrically connected respectively to the power transmission interface.

Further, the upper protecting frame comprises at least a first support rod, and the lower protecting frame comprises a plurality of second support rods, with the number of the second support rods being the same as or different from that of the first support rods. The first support rod and the second support rod correspond to each other/or do not correspond one-to-one. The number of the lifting mechanisms is the same as or different from that of the first support rods, and the lifting mechanism is respectively disposed at the intersection position of the first support rod with the second support rod, or at the intersection position of the upper protecting frame with the lower protecting frame.

Further, the upper protecting frame comprises two symmetrically disposed first support rods, and the lower protecting frame comprises two symmetrically disposed second support rods, with the first support rods and the second support rods corresponding one to another. The number of the lifting mechanisms is two, and the two lifting mechanisms are each respectively disposed at an intersection of one of the first support rods with one of the second support rods.

Further, the upper protecting frame comprises three spaced apart first support rods, and the lower protecting frame comprises three spaced apart second support rods, the first support rods and the second support rods corresponding to one another. The number of the lifting mechanisms is three, and the three lifting mechanisms are each respectively disposed at an intersection of one of the first support rods with one of the second support rods.

Further, the upper protecting frame comprises four first support rods, and a spacing in-between the four first support rods being the same or different. The lower protecting frame comprises four second support rods, and a spacing in-between the four second support rods being the same or different, and the four first support rods and the four second support rods correspond to one another. The number of the lifting mechanisms is four, and the four lifting mechanisms are each respectively disposed at an intersection of one of the four first support rods with one of the four second support rods.

Further, the barrel-shaped protecting frame comprises two semi-ring protecting shelves.

The upper protecting frame console, the middle protecting frame support and the bottom support are separately divided each into a left part and a right part, with a left part and a right part being symmetric and matching each other; the two semi-ring protecting shelves are comprised of left and right parts of the upper protecting frame console, of the middle protecting frame support and of the bottom support, as well as comprised of the first support rod and the second support rod.

An end each of the two semi-ring protecting shelves is connected to one another via the rotating rod. The two semi-ring protecting shelves are rotated around the rotating rod for closing and opening the barrel-shaped protecting frame and the protecting cover.

Further, the medical radiation protection device further comprises an opening and closing system. The opening and closing system includes a rotating rod, an opening and closing motor and an opening and closing control device. The rotating rod is disposed in a vertical direction of the barrel-shaped protecting frame, and the opening and closing motor is disposed on the rotating rod, and at least a portion of the barrel-shaped protecting frame is rotated around the rotating rod for opening and closing the protecting cover.

Further and preferably, an anti-pinch device is also provided on a face for switching and closing of the two semi-ring protecting shelves.

Further, the opening and closing control device comprises a magnetic switch, a voice control device, or a gesture control device.

Further, the medical radiation protection device further comprises a power switch and a power indicator device, the power switch and the power indicator device being mounted on the upper protecting frame.

Further, the protecting cover comprises an upper protecting frame cover and a lower protecting frame cover. The upper protecting frame cover surrounds the upper protecting frame in a full circle, and the lower protecting frame cover surrounds the lower protecting frame in a full circle, a lower portion of the lower protecting frame cover extends to a horizontal floor; an outer side of an upper portion of the lower protecting frame cover closely fits an inner side of the upper protecting frame cover, a sum of the height of the upper protecting frame cover and that of the lower protecting frame cover is greater than the height of the medical radiation protection device.

Further, the barrel-shaped protecting frame comprises two semi-ring protecting shelves. An end each of the two semi-ring protecting shelves is connected to one another via the rotating rod. The two semi-ring protecting shelves are rotated around the rotating rod for closing and opening the barrel-shaped protecting frame and the protecting cover. An anti-pinch device is further provided on a face for switching and closing of the two semi-ring protecting shelves. The anti-pinch device can effectively prevent pinching the surgeon doctor.

Further, the protecting cover comprises an upper protecting frame cover and a lower protecting frame cover. The upper protecting frame cover surrounds the upper protecting frame in a full circle, and the lower protecting frame cover surrounds the lower protecting frame in a full circle, with a lower portion thereof extending to a horizontal floor, and an outer side of an upper portion of the lower protecting frame cover closely fits an inner side of the upper protecting frame cover. The sum of the height of the upper protecting frame cover and that of the lower protecting frame cover is greater than the height of the medical radiation protection device.

Further, the upper protecting frame cover has an inner protecting cover and an outer protecting cover, respectively fixedly connected to an inner side wall and an outer side wall of the upper protecting frame. The lower protecting frame cover has an inner protecting cover and an outer protecting cover, respectively fixedly connected to an inner side wall and an outer side wall of the lower protecting frame. The distance between the inner protecting cover and the outer protecting cover of the upper protecting frame cover is greater than the distance between the inner protecting cover and the outer protecting cover of the lower protecting frame cover, permitting insertion of the lower protecting frame cover into the upper protecting frame cover for sliding movement.

Further, the upper end of the outer protecting cover of the upper protecting frame cover is further fixedly connected to a hook side or a loop side of a hook and loop, with the corresponding loop side or the hook side of the hook and loop being sewn at a corresponding position on an upper portion of the outer side of the inner protecting cover of the upper protecting frame cover; a suspension collar is respectively sewn at the upper end of the inner protecting cover of the upper protecting frame cover and at the junction of the outer protecting cover with the hook and loop thereof.

The upper end of the outer protecting cover of the lower protecting frame cover is fixedly connected to a hook side or a loop side of a hook and loop, with the corresponding loop side or the hook side of the hook and loop being sewn at a corresponding position on an upper portion of the outer side of the inner protecting cover of the lower protecting frame cover; a suspension collar is respectively sewn at the upper end of the inner protecting cover of the lower protecting frame cover and at the junction of the outer protecting cover with the hook and loop thereof;

Further, the medical radiation protection device further comprises a fixed strip and a column; the column has an inverted "L" shape, or an "arc" shape, or a "T" shape, the columns are disposed along both sides of the upper end surface of the upper protecting frame support, with the fixed strip passing through the suspension collar of the upper protecting frame cover and is fixedly suspended in the inner side of the column;

The columns are also arranged along both sides of the upper end surface of the middle protecting frame support, with the fixed strip passing through the suspension collar of the lower protecting frame cover and is fixedly suspended in the inner side of the column.

Further, the column may also be annular, with the fixed strip sequentially passing through the suspension collar and the annular column respectively to fix the protecting cover on the protecting frame.

As another embodiment for fixing the protecting cover onto the upper protecting frame console and the middle protecting frame support, a fixed strip together with a sleeve supporting the fixed strip is further comprised; the fixed strip is provided with a fixing pin hole; subsequent to passing the suspension collar of the upper protecting frame cover via the fixed strip, a screw is driven through the fixing pin hole and the sleeve to fix the fixed strip onto the upper protecting frame console. On the other hand, subsequent to passing the suspension collar of the lower protecting frame cover via the fixed strip, a screw is driven through fixing pin hole and the sleeve to fix the fixed strip onto the middle protecting frame console.

As another embodiment for fixing the protecting cover onto the upper protecting frame console and the middle protecting frame support, a middle portion of the fixed strip is arched upwardly into a large arch shape, and the left and the right end each of the fixed strip is respectively provided with two fixing pin holes, the position between the two fixing pin holes at the left end of the fixed strip is arched upwardly, and the position between two fixing pin holes at the right end of the fixed strip is upwardly arched into a small arch shape. The hook side or the loop side of the hook and loop on the upper end of the upper protecting frame cover passes through the large arch in the middle portion of the fixed strip, and is fixed to the loop side or the hook side of the hook and loop on the outer side of the upper protecting frame cover. The fixed strip is fixed on the upper protecting frame console by passing the suspension collar on the upper protecting frame cover through the small arch shape on the left and the right side of the fixed strip respectively, and by driving a screw respectively through the pin hole on either side of the fixed strip. The hook side or the loop side of the hook and loop on the upper end of the lower protecting frame cover passes through the large arch in the middle portion of the fixed strip, and is fixed to the loop side or the hook side of the hook and loop on the outer side of the lower protecting frame cover. The fixed strip is fixed on the middle protecting frame support by passing the suspension collar on the lower protecting frame cover through the small arch shape on the left and the right side of the fixed strip respectively, and by driving a screw through the pin hole on either side of the fixed strip.

Further, plural universal casters are provided on the bottom of the lower protecting frame.

Further, 3-5 (4 is preferable) uniformly or unevenly distributed universal casters are provided on the bottom of the lower protecting frame. The universal caster comprises a universal wheel and a universal wheel support frame, with an end of the universal wheel support frame being connected to the universal wheel, and another end thereof being fixedly connected to the bottom of the lower protecting frame. The angle between the universal wheel support frame and the outer side wall of the lower protecting frame is greater than or equal to 90 degrees, with the universal wheel being extended to the outer side of the lower protecting frame under support of the universal wheel support frame.

Further, on the bottom of the lower protecting frame cover is provided a foot operation opening and a universal wheel support frame mounting hole, and the foot operation opening is in a shape of an arch, a square, a semicircle, or an irregular shape.

Further, the door panel comprises a left door panel and a right door panel. The right end surface of the left door panel has an L shape in a horizontal direction, and the left end surface of the corresponding right door panel has an inverted L shape in a horizontal direction. The right end of the left door panel is embedded and sealed in the left end of the right door panel, for blocking radiation from entering the medical radiation protection device via the junction of the left door panel with the right door panel.

Further, the barrel-shaped protection frame is made of stainless steel, iron, gold, silver, copper, aluminum, zinc or manganese. The protecting cover is made of lead, lead material, iron, concrete, lead rubber, radiation-proof inorganic lead glass, radiation-proof organic lead glass or fiber reinforced plastic composite protective material.

Further, the protecting cover (102) comprises a layer of X-ray protective material.

The disclosure further provides a medical radiation protection device, comprising a barrel-shaped protection device, a lifting system and an opening and closing system. The barrel-shaped protection device comprises an upper protection device and a lower protection device. The inner diameter of the upper protection device is greater or smaller than the inner diameter of the lower protection device. The upper protection device and the lower protection device are connected to each other, with the upper protection device being closely and fittingly sliding along the outer side wall or the inner side wall of the lower protection device under action of the lifting system. An X-ray protective material layer is disposed in the inner side, in the outer side or on the side wall of the barrel-shaped protection device. The lifting system comprises a lifting motor, a lifting mechanism and a lifting control device. The opening and closing system includes a rotating rod, an opening and closing motor and an opening and closing control device.

Advantageous effects of embodiments of the present disclosure are as follows:

1) The protection device does not need to be worn on a surgeon doctor, thus greatly reducing the burden therefor as well the adverse effects on the lumbar spine and lower extremity joints thereof, and being conducive to the doctor's health.

2) By increasing thickness of the protecting cover, protective effect is significantly increased, and damage of the X-ray to the surgeon doctor is reduced. Employment of the protection device is simple and convenient; opening, closing and lifting of the device is realized merely via the control switch and the lifting motor, facilitating entrance and exit for the surgeon doctor, and accommodating any height of the surgeon doctor.

3) By means of manipulating the universal caster, the surgeon doctor can maneuver with ease during operation, thus ensuring smooth proceeding of the operation.

4) The universal caster features an outward protrusion, is located on outskirts of the protection device to enhance stability.

5) On one hand, the lower protecting frame cover extends to the floor, constituting effective foot protection for the surgeon doctor. On the other hand, the bottom of the lower protecting frame cover has an arch-shaped, square, semi-circular, or irregular-shaped foot operation opening for the surgeon doctor to extend their feet to operate other machines, such as a pedal of an X-ray machine.

BRIEF DESCRIPTION OF THE DRAWINGS

The specific embodiments of the present disclosure will be further enunciated hereunder with reference to the accompanying drawings.

DETAILED DESCRIPTION OF THE INVENTION

Figure 1:
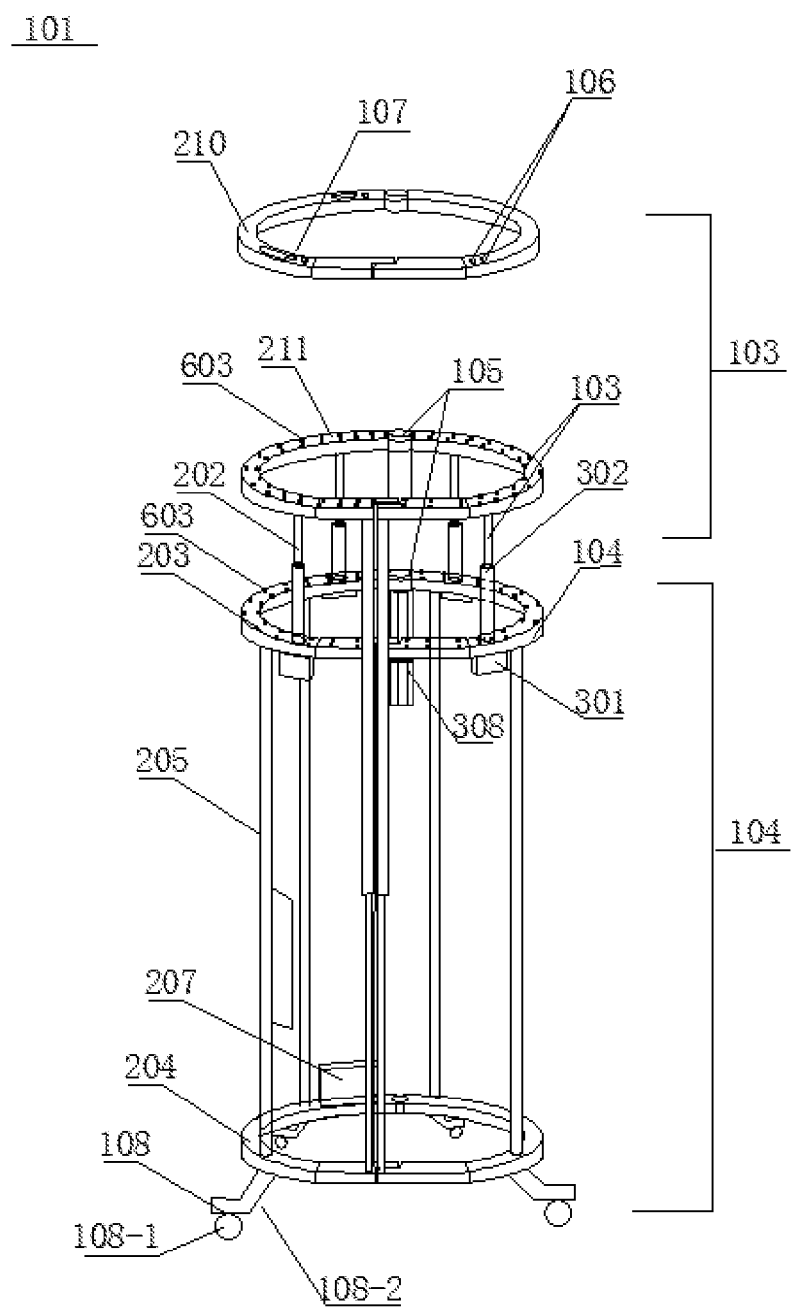
FIG. 1 is a schematic perspective view of the barrel-shaped protecting frame of the medical radiation protection device.
Figure 2:
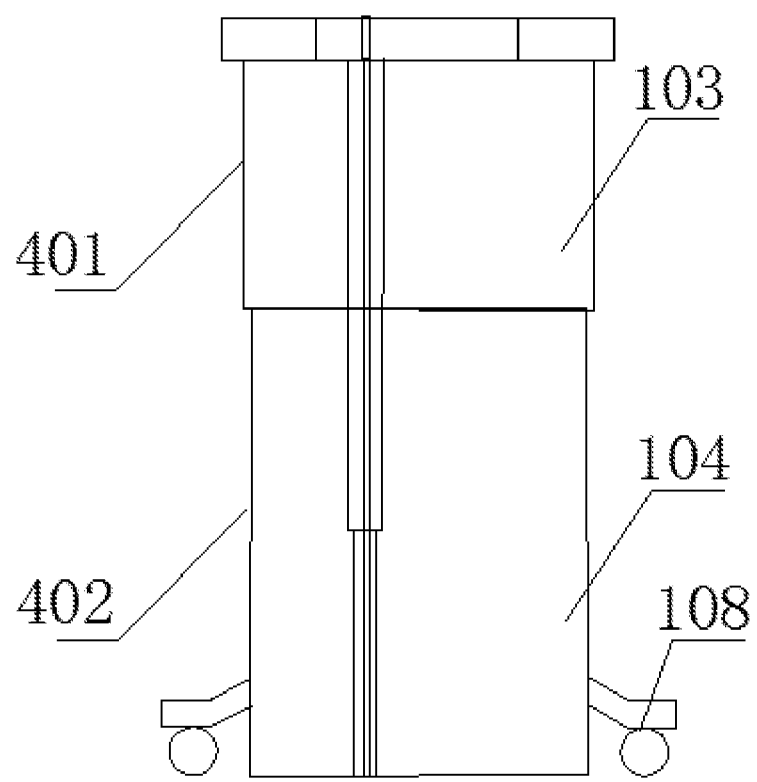
FIG. 2 is a schematic front view of the medical radiation protection device.
Figure 14:
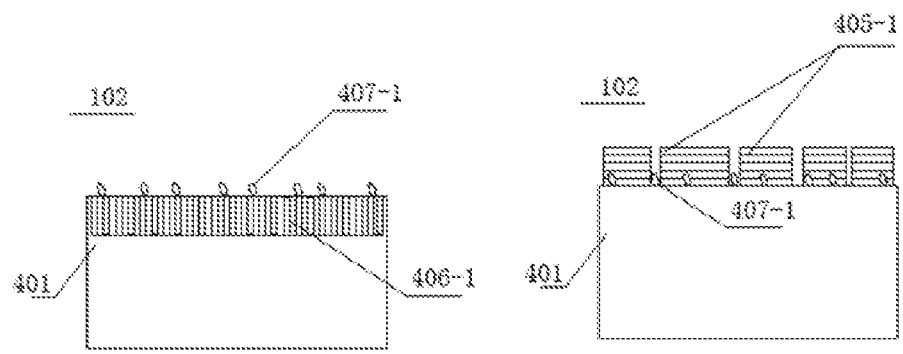
FIG. 14 is a schematic diagram of the protecting cover.
Figure 14:
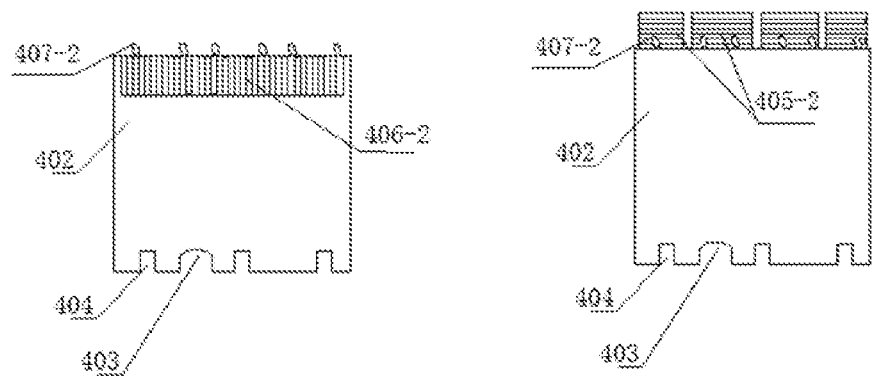

Embodiment 1: As shown in FIG. 1, FIG. 2, and FIG. 14, the medical radiation protection device comprises a barrel-shaped protecting frame 101 and a protecting cover 102. The barrel-shaped protecting frame 101 comprises an upper protecting frame 103 and a lower protecting frame 104. Adoption of the barrel-shaped protecting frame saves space for operation and is convenient for interventional operations conducted by a surgeon doctor. The surgeon doctor conducting the interventional operation in the barrel-shaped protection device can rotate 360 degrees to meet requirement of the clinical interventional operation.

The medical radiation protection device further comprises a lifting system, the lifting system comprising a lifting motor 301, a lifting mechanism 302 and a lifting control device 106. The upper protecting frame 103 is connected to the lower protecting frame 104 via the lifting mechanism 302. The upper protecting frame 103 is supported by the lower protecting frame 104 to move up and down under action of the lifting mechanism. The protecting cover 102 is disposed to encircle around an inner side wall and/or an outer side wall of the barrel-shaped protecting frame 101. The lifting control device 106 comprises a button switch, a voice control device or a gesture control device; the button switch, the voice control device or the gesture control device are installed on the upper protection frame 103. The lifting mechanism allows a protective portion of the medical radiation protection device to go up or down to suit interventional doctors of various physical heights, as well as to meet actual needs in the process of a surgical operation. Further, employment of voice control or gesture control makes operation of the lifting system easier and more convenient.

As shown in FIG. 1, the upper protecting frame 103 comprises an upper protecting frame console 201 and at least a first support rod 202. The upper protecting frame console 201 comprises an upper protecting frame console panel 210 and an upper protecting frame console support frame 211, and the upper protecting frame console panel 210 is fixed on the upper protecting frame console support frame 211 via a screw. The first support rod 202 is fixedly connected to a lower bottom surface of the upper protecting frame console 201 and to the lifting mechanism 302, and is under control of the lifting mechanism 302 for up or down movement; the lower protecting frame 104 comprises a middle protecting frame support 203, a bottom support 204 and a second support rod 205, with the middle protecting frame support 203 and the bottom support 204 being fixedly connected via the second support rod 205. In contrast to other support structures, such as a support wall, adoption of the support rods not only reduces weight of the whole device, but it also makes raising and lowering of the upper frame console easier.

The lifting mechanism 302 and the lifting motor 301 are fixed on the middle protecting frame support 203.

The upper protecting frame console 201, the middle protecting frame support 203 and the bottom support 204 have a same cross-sectional shape; the upper protecting frame console 201 is provided with a door panel 206 along a secant direction, and a front and a rear side each of the door panel 206 is in planar shape; correspondingly, the middle protecting frame support and the bottom support each is respectively provided with a door panel along a secant direction, and a front and a rear side each of the door panel is in planar shape. Provision of the planar door panel fits the medical radiation protection device of the present disclosure closer to the operating table, thus shortening distance between the surgeon doctor and the patient.

The medical radiation protection device further comprises a charging device 207, with the charging device 207 comprising a charging interface, a rechargeable battery and a power transmission interface, and being mounted on the lower protecting frame 104. The lifting motor 301 is electrically connected to the power transmission interface. Provision of the charging device allows the medical radiation protection device of the present disclosure to move freely, not confined to a limited range.

Figure 5:
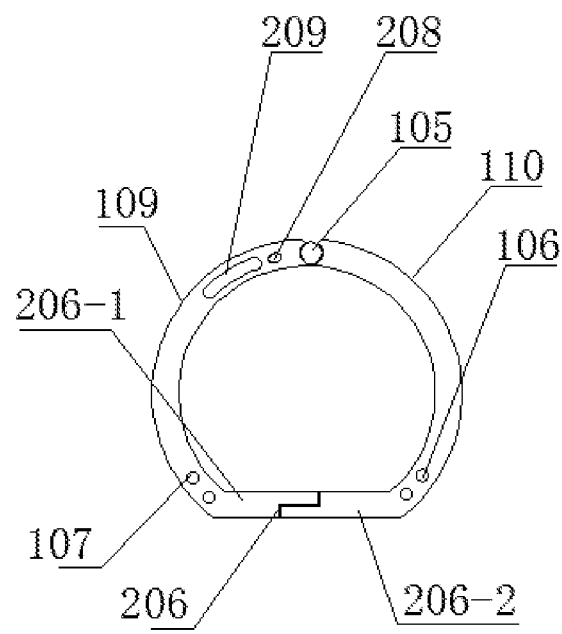
FIG. 5 is a schematic top view of the medical radiation protection device in a closed state.
Figure 6:
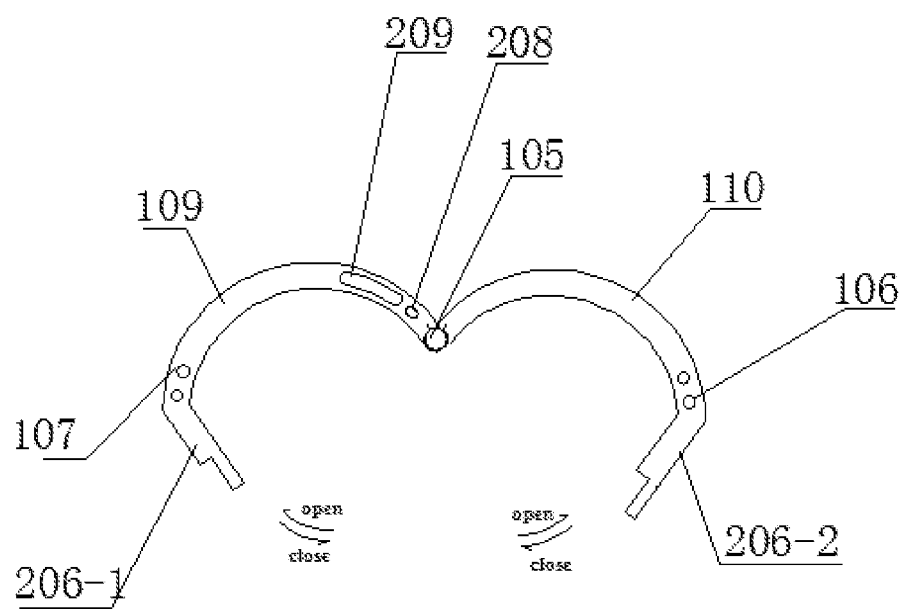
FIG. 6 is a schematic top view of the medical radiation protection device in an opened state.

As shown in FIG. 1, FIG. 5, and FIG. 6, the medical radiation protection device further comprises a power switch 208 and a power indicator device 209, with the power switch 208 and the power indicator device 209 being mounted on the upper protecting frame console 201; the power switch 208 and the power indicator device 209 are electrically connected respectively to the power transmission interface. The power indicator device can effectively indicate a power status, remind charging when needed, and avoid operation failure due to insufficient power.

Figure 12:
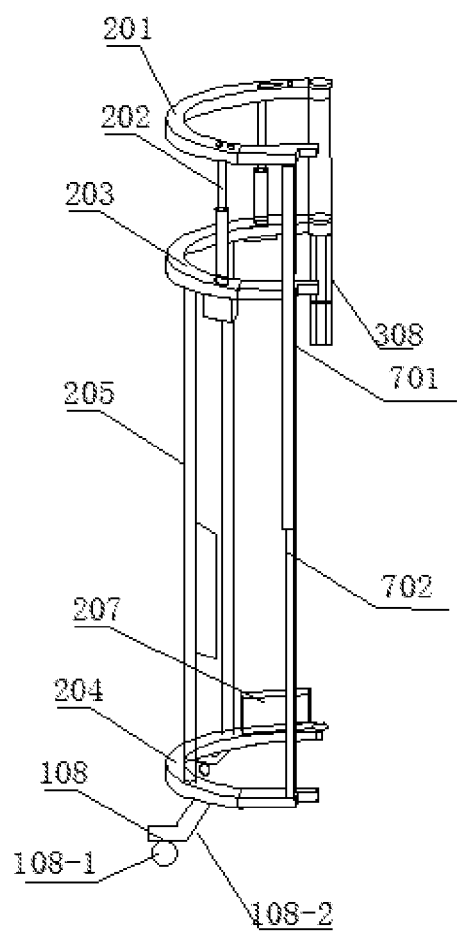
FIG. 12 is a schematic view showing a left side structure of the semi-ring protecting shelf of the present disclosure.
Figure 13:
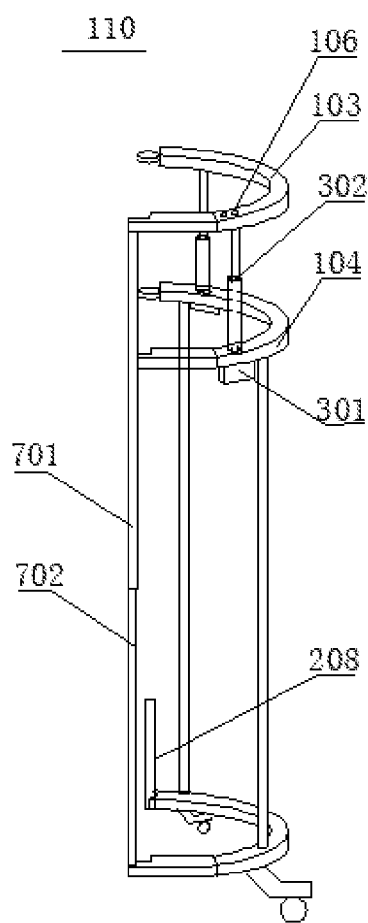
FIG. 13 is a schematic view showing a right side structure of the semi-ring protecting shelf of the present disclosure.

As shown in FIG. 12 and FIG. 13, the barrel-shaped protecting frame 101 comprises a left and a right semi-ring protecting shelf 109, 110.

The upper protecting frame console 201, the middle protecting frame support 203 and the bottom support 204 are separately divided each into a left part and a right part, with the left part and the right part being symmetric and matching each other; the two semi-ring protecting shelves 109,110 are comprised respectively of left and right parts of the upper protecting frame console 201, of the middle protecting frame support 203 and of the bottom support 204, as well as comprised of the first support rod 202 and the second support rod 205.

An end each of the two semi-ring protecting shelves 109, 110 is connected to one another via the rotating rod 105; the two semi-ring protecting shelves 109, 110 are rotated around the rotating rod 105 for closing and opening the barrel-shaped protecting frame 101 and the protecting cover 102. The left and the right semi-ring protecting shelves are rotated around the rotating rod so that they can be opened and closed for easy access to the surgeon doctor.

As shown in FIG. 1 and FIG. 5, the medical radiation protection device further comprises an opening and closing system. The opening and closing system includes a rotating rod 105, an opening and closing motor 308, and an opening and closing control device 107. The rotating rod 105 is disposed vertically in respect of the barrel-shaped protecting frame 101, and the opening and closing motor is disposed on the rotating rod 105, and at least a portion of the barrel-shaped protecting frame 101 is rotated around the rotating rod 105 for opening and closing the protecting cover 102. The opening and closing motor and the opening and closing control device are employed to control rotation of the left and the right semi-ring protecting shelves around the rotating rod, thereby reducing physical strength input from the surgeon doctor, and make operation simple and convenient.

An anti-pinch device is further provided on a face for switching and closing of the two semi-ring protecting shelves 109, 110. The anti-pinch device can effectively prevent pinching the surgeon doctor resulting from incorrect operation.

The opening and closing control device 107 includes a magnetic switch, a voice control device, or a gesture control device. Voice or gesture control is simple and convenient.

As shown in FIG. 2 and FIG. 14, the protecting cover 102 comprises an upper protecting frame cover 401 and a lower protecting frame cover 402. The upper protecting frame cover 401 surrounds the upper protecting frame in a full circle, and the lower protecting frame cover 402 surrounds the lower protecting frame in a full circle. A lower portion of the lower protecting frame cover 402 extends to the horizontal floor, and the outer side of an upper portion of the lower protecting frame cover 402 closely fits the inner side of the upper protecting frame cover 401. The sum of the height of the upper protecting frame cover 401 and that of the lower protecting frame cover 402 is greater than the height of the medical radiation protection device. The outer side of an upper portion of the lower protecting frame cover 402 closely fits the inner side of the upper protecting frame cover 401. The sum of the height of the upper protecting frame cover 401 and that of the lower protecting frame cover 402 is greater than the height of the medical radiation protection device. Employment of the upper protecting frame cover together with the lower protecting frame cover realizes raising and lowering of the device of the present disclosure on one hand, and on the other hand no protection pitfall is created.

The upper protecting frame cover 401 has an inner protecting cover and an outer protecting cover, respectively fixedly connected to an inner side wall and an outer side wall of the upper protecting frame 103. The lower protecting frame cover 402 has an inner protecting cover and an outer protecting cover, respectively fixedly connected to an inner side wall and an outer side wall of the lower protecting frame 104. A distance between the upper protecting frame covers fixed on the inner side wall and the outer side wall of the upper protecting frame is greater than a distance between the lower protecting frame covers fixed on the inner side wall and the outer side wall of the lower protecting frame, permitting insertion of the lower protecting frame cover 402 into the upper protecting frame cover 401 for sliding movement. Adoption of the inner and the outer protecting covers achieves better radiation blocking effect better.

As shown in FIG. 14, an upper end of the outer protecting cover of the upper protecting frame cover 401 is further fixedly connected to a hook side or a loop side 405-1 of a hook and loop, with the corresponding loop side or the hook side 406-1 of the hook and loop being sewn at a corresponding position on an upper portion of an outer side of the inner protecting cover of the upper protecting frame cover 401; a suspension collar 407-1 is respectively sewn at an upper end of the inner protecting cover of the upper protecting frame cover 401 and at a junction of the outer protecting cover with the hook and loop thereof.

As shown in FIG. 14, an upper end of the outer protecting cover of the lower protecting frame cover 402 is fixedly connected to a hook side or a loop side 405-2 of a hook and loop, with the corresponding loop side or the hook side 406-2 of the hook and loop being sewn at a corresponding position on an upper portion of the outer side of the inner protecting cover of the lower protecting frame cover 402; a suspension collar 407-2 is respectively sewn at the upper end of the inner protecting cover of the lower protecting frame cover 402 and at a junction of the outer protecting cover with the hook and loop thereof.

Figure 19:
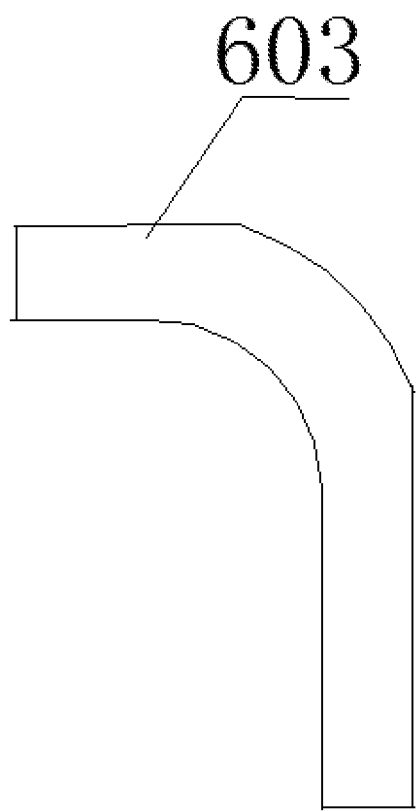
FIG. 19 is a schematic diagram of the column.
Figure 20:
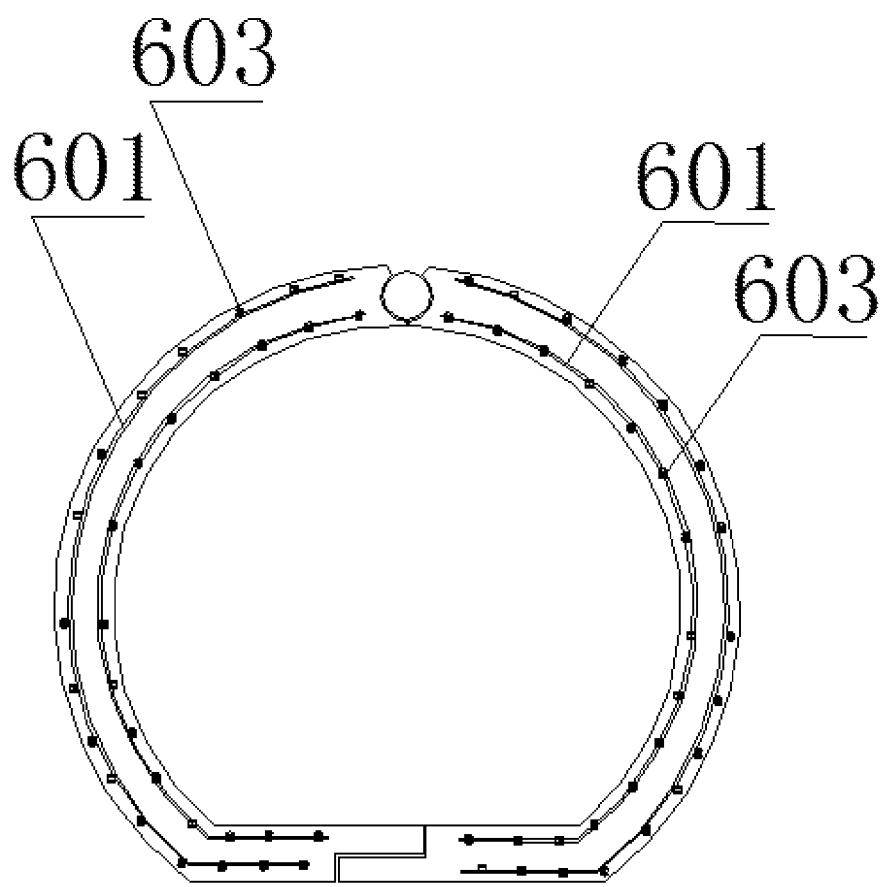
FIG. 20 is a schematic diagram of the middle protecting frame support in columnar style fixing the fixed strip.

As shown in FIG. 1, FIG. 19 and FIG. 20, the medical radiation protection device further comprises a fixed strip 601 and a column 603. The column 603 has an inverted "L" shape, or an "arc" shape, or a "T" shape. The columns 603 are disposed along both sides of the upper end surface of the upper protecting frame support 211, with the fixed strip 601 passing through the suspension collar of the upper protecting frame cover 401 and is fixedly suspended in the inner side of the column 603; The columns 603 are disposed along both sides of the upper end surface of the middle protecting frame support 203, with the fixed strip 601 passing through the suspension collar of the lower protecting frame cover 402 and is fixedly suspended in the inner side of the column 603. The column and the fixed strip of the disclosure are easy to manipulate, mount and dismount for fixing the protecting cover. Moreover, with provision of the hook and loop, fixation of the inner and the outer protecting cover is further strengthened and has a better effect.

Figure 15:
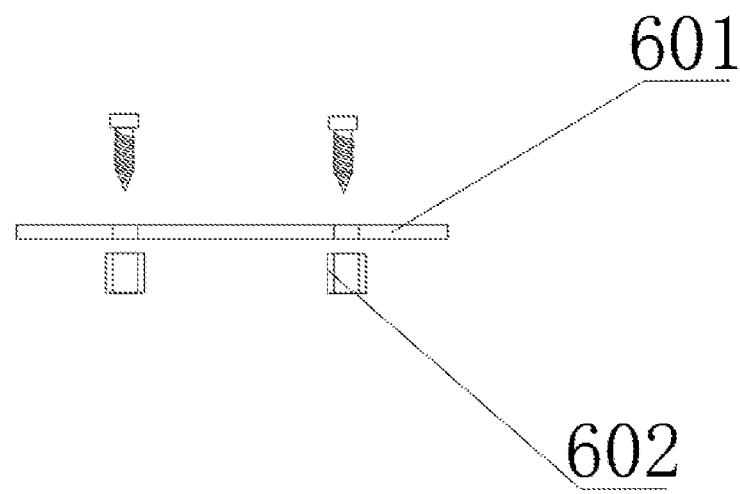
FIG. 15 is a schematic diagram of the fixed strip.
Figure 16:
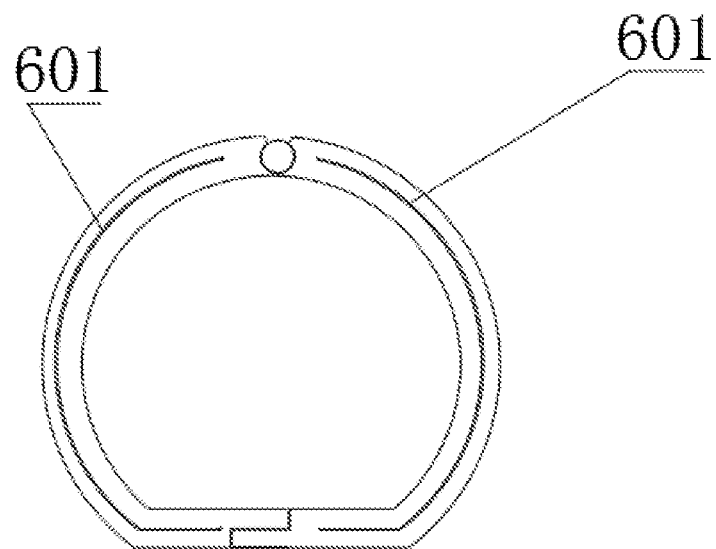
FIG. 16 is a schematic top view showing the fixed strip fixed to the middle protecting frame support.

As another embodiment for fixing the protecting cover onto the upper protecting frame console and the middle protecting frame support, as is shown in FIG. 15, a fixed strip 601 is further comprised for fixing the protecting cover to the upper protecting frame console 201 and the middle protecting frame support 203, with a sleeve 602 supporting the fixed strip 601; the fixed strip 601 is provided with a fixing pin hole. Subsequent to passing the suspension collar of the upper protecting frame cover 401 through the fixed strip 601, a screw is driven through the fixing pin hole, and then through the sleeve to fix the fixed strip 601 on the upper protecting frame console 201; subsequent to passing the suspension collar of the upper protecting frame cover 402 through the fixed strip 601, a screw is driven through the fixing pin hole, and then through the sleeve 602 to fix the fixed strip 601 on the middle protecting frame console 203.

Figure 17:
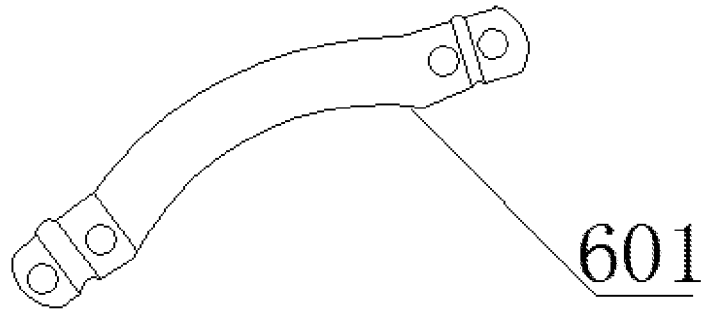
FIG. 17 is a schematic diagram of another embodiment of the fixed strip.
Figure 18:
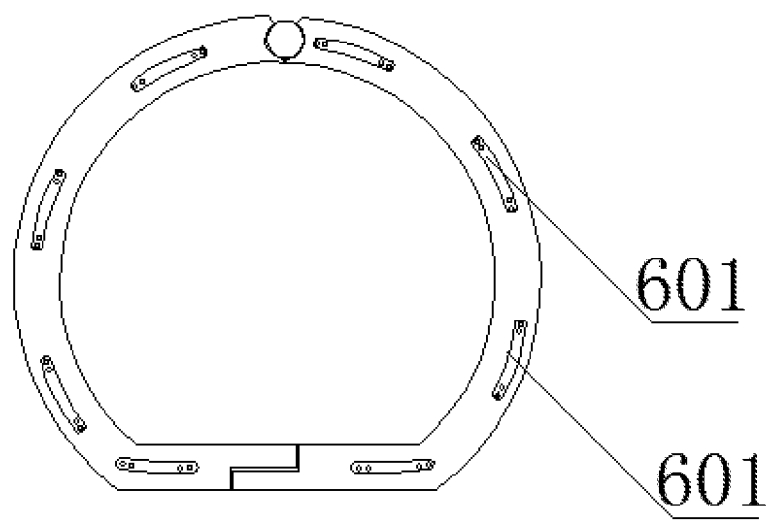
FIG. 18 is a schematic top view of yet another embodiment of the fixed strip fixed to the middle protecting frame support.

As another embodiment for fixing the protecting cover to the upper protecting frame console and the middle protecting frame support, as shown in FIG. 17 is the fixed strip 601 for fixing the protecting cover to the upper protecting frame console 201 and the middle protecting frame support 203. A central portion of the fixed strip 601 is arched upwardly into a large arch shape, and the left and the right end each of the fixed strip 601 is respectively provided with two fixing pin holes, a position between the two fixing pin holes at the left end of the fixed strip 601 is arched upwardly into a small arch shape, and a position between the two fixing pin holes at the right end of the fixed strip 601 is upwardly arched into another small arch shape. The hook side or the loop side of the hook and loop 405-1 on the upper end of the upper protecting frame cover 401 passes through the large arch in the middle of the fixed strip 601, and is fixed to the loop side or the hook side of the hook and loop on the outer side of the upper protecting frame cover 401. The suspension collar 407-1 on the upper protecting frame cover 401 passes through the small arch shape each on the left and right sides of the fixed strip 601 respectively, and the fixed strip 601 is fixed on the upper protecting frame console 201 by means of driving a screw through the pin hole each on either side of the fixed strip 601. As shown in FIG. 17 and FIG. 18, the hook side or the loop side of the hook and loop on the upper end of the lower protecting frame cover 402 passes through the large arch in the middle of the fixed strip 601, and is fixed to the loop side or the hook side of the hook and loop 406-2 on the outer side of the lower protecting frame cover 402. The suspension collar 407-2 on the lower protecting frame cover 402 passes through the small arch shape each on the left and the right side of the fixed strip 601 respectively, and the fixed strip 601 is fixed on the middle protecting frame support 203 by means of driving a screw through the pin hole each on either side of the fixed strip 601.

Further, as shown in FIG. 12 and FIG. 13, a door strip is further comprised. The door strip comprises an upper door strip 701 and a lower door strip 702. The upper door strip 701 is fixedly mounted on the upper protecting frame 103, the lower door strip 702 is fixedly mounted on the lower protecting frame 104, and the lower door strip 702 is inserted into the upper door strip 701 and slides therein. The upper protecting frame cover 401 surrounds the upper protecting frame in a full circle, with each end of the upper protecting frame cover 401 being respectively fixed on the upper door strip. The lower protecting frame cover 402 surrounds the lower protecting frame in a full circle, with each end of the lower protecting frame cover 402 being respectively fixed on the lower door strip.

As shown in FIG. 1, 3-5 universal casters 108 are arranged on the bottom of the bottom support 204 has, with each universal caster comprising a universal wheel 108-1 and a universal wheel support frame 108-2, one end of the universal wheel support frame 108-2 being connected to the universal wheel 108-1, while another end thereof being fixedly connected to the bottom of the bottom support 204. The angle between the universal wheel support frame 108-2 and the outer side wall of the bottom support 204 is greater than or equal to 90 degrees, with the universal wheel 108-1 being extended exterior to the outer side of the lower protecting frame 104 under support of the universal wheel support frame 108-2. The universal wheel of the present disclosure enables the device of the present disclosure to be capable of being rotated 360 degrees, with the any degree of angle granting a high degree of adaptability to the clinical operation. Arrangement of the universal wheel of the present disclosure exterior to the outer side of the lower protecting frame 104 increases moment of the supporting force and stability, and as contact with feet of the surgeon doctor is prevented, range of maneuvering thereof is increased As shown in FIG. 14, on the bottom of the lower protecting frame cover 402 is provided with a foot operation opening 403 and a universal wheel support frame mounting hole 404, with the foot operation opening 403 having an arch shape, a square shape, a semicircular shape or other irregular shape. The foot operation opening 403 provided by the present disclosure facilitates operation of other devices by the surgeon doctor, as is needed for an interventional operation.

As shown in FIG. 5 and FIG. 6, the door panel 206 comprises a left door panel 206-1 and a right door panel 206-2. The right end surface of the left door panel 206-1 has an L shape in the horizontal direction; the left end surface of the corresponding right door panel 206-2 has an inverted L shape in the horizontal direction. The right end of the left door panel 206-1 is embedded and sealed in the left end of the right door panel 206-2, for blocking radiation from entering the medical radiation protection device via the junction of the left door panel 206-1 with the right door panel 206-2. The design of staggered embedding of the left and the right door panels prevents radiation from entering the device of the present disclosure due to possible cracks between the door-panels.

As shown in FIG. 1, the number of the first support rods 202 is 3-4, correspondingly the number of sets of the lifting system 302 is 3-4. The number of the second support rods 205 is 3-4. The rechargeable battery is a lithium battery, a lead acid battery, or a nickel hydrogen battery.

The barrel-shaped protecting frame 101 is made of stainless steel, iron, gold, silver, copper, aluminum, zinc or manganese, and the protecting cover 102 is made of lead, lead material, radiation-proof inorganic lead glass, radiation-proof organic lead glass or fiber reinforced plastic composite protective material. The protecting cover 102 comprises a layer of X-ray protective material.

Embodiment 2: referring to FIG. 1, FIG. 2 and FIG. 14, the present disclosure provides the medical radiation protection device 100 comprising the barrel-shaped protecting frame 101 and the protecting cover 102. The barrel-shaped protecting frame 101 comprises the upper protecting frame 103 and the lower protecting frame 104. The upper protecting frame 103 is connected to the lower protecting frame 104, and the upper protecting frame 103 can move up and down along the lower protecting frame 104. In one embodiment, the barrel-shaped protecting frame 101 is made of stainless steel. The barrel-shaped protecting frame 101 may also be made of metal and alloys thereof, such as iron, gold, silver, copper, aluminum, zinc, manganese, etc. The barrel-shaped protecting frame 101 may also be made of wood.

The protecting cover 102 is disposed on the side wall of the barrel-shaped protecting frame 101. The protecting cover 102 is made of an X-ray protective material. The X-ray protective material comprises lead, lead materials, lead rubber, radiation-proof inorganic lead glass, radiation-proof organic lead glass, or fiber reinforced plastic composite protective materials. A surgeon doctor employing the protecting cover stands within the protecting cover 102 so as to be shielded against X-ray. In one embodiment, the lowermost end of the protecting cover 102 reaches the ground.

The barrel shape in the present embodiment should be understood in a broad sense, that is, the barrel-shaped protecting frame 101 and the protecting cover 102 form a shape sealed within the side thereof. For example, it may be a hollow cylinder, a hollow elliptical cylinder, a hollow prism, a hollow polygonal cylinder or other irregularly shaped hollow cylinder. As perceived from the perspective of the top view thereof, the cross-sectional shape thereof may be a circle, an ellipse, a polygon (a quadrangle, a pentagon, a hexagon, etc.), as well as other irregular shapes.

In another embodiment, the side walls formed by the protecting cover 102 do not constitute a complete enclosure. For example, on some cases, radiation appears only in front of the surgeon doctor, not in the rear or in the sides thereof. Therefore, the protecting cover 102 only needs to block radiation in front of the surgeon doctor. The protecting cover 102 may be a non-enclosed hollow cylinder, a hollow polygonal cylinder, or a hollow irregular cylinder.

Figure 3:
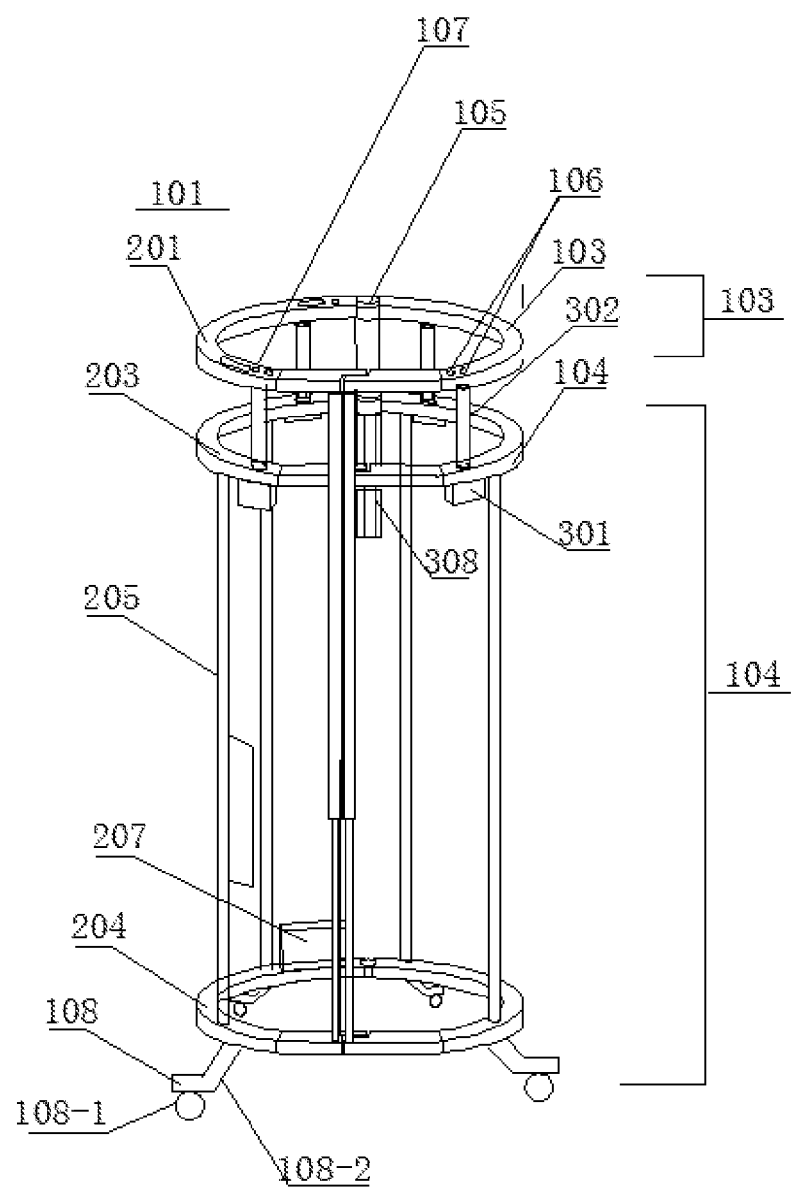
FIG. 3 is a schematic diagram of the barrel-shaped protecting frame of the medical radiation protection device at an initial height.
Figure 4:
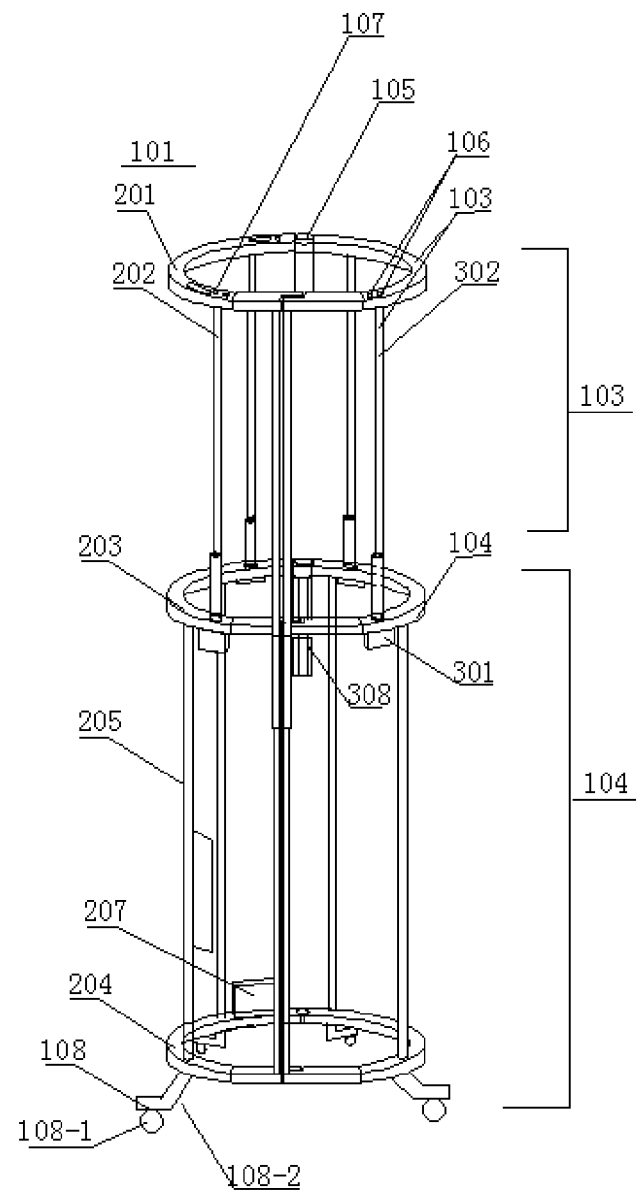
FIG. 4 is a schematic diagram of the medical radiation protection device with height adjustment (height increasing)

In one embodiment, the medical radiation protection device 100 further comprises the lifting system for raising or lowering the upper protecting frame 103 along the lower protecting frame 104. Referring to FIG. 3 and FIG. 4, the lifting system comprises the lifting motor 301, the lifting mechanism 302 and the lifting control device 106. The upper protecting frame 103 is connected to the lower protecting frame 104 via the lifting mechanism 302. The lifting control device 106 may be a push button. Specifically, the lifting control device 106 comprises two push buttons; one push button gives rise to rising of the lifting mechanism under action of the lifting motor, while the other push button gives rise to lowering of the lifting mechanism under action of the lifting motor. In another embodiment, the lifting control device 106 comprises only one push button. One press of the button raises the lifting mechanism; a second press lowers the lifting mechanism; a third press raises the lifting mechanism . . . and so on, alternatively raising and lowering the lifting mechanism. In another embodiment, the lifting control device 106 may be a voice control device or a gesture control device. The surgeon doctor controls the lifting motor 301 by a preset voice or gesture, raising or lowering the lifting mechanism 302 by means of the lifting motor 301. The lifting control device 106 may be disposed at any position of the medical radiation protection device 100. For example, the lifting control device 106 may be disposed on the upper protecting frame 103 or the lower protecting frame 104 to facilitate user operation. With the raising of the lifting mechanism 302, the upper protecting frame 103 is moved upward along the lower protecting frame 104; with the lowering of the lifting mechanism 302, the upper protecting frame 103 is moved downward along the lower protecting frame 104. Therefore, the surgeon doctor raises or lowers the upper protecting frame 103 by means of the lifting mechanism 302 according to the height thereof and/or other prerequisites.

In one embodiment, the lifting control device 106 comprises two separate push buttons. The two push buttons are disposed on the upper protecting frame console 201 at the top of the upper protecting frame 103. The two push buttons are marked with "Up" and "Down" respectively to prevent wrong touching.

In one embodiment, the upper protecting frame 103 comprises two first support rods disposed substantially symmetrically; the lower protecting frame comprises two second support rods disposed substantially symmetrically. The first support rod and the second support rod correspond one to the other. Two lifting mechanisms 302 are respectively disposed each at the intersection of one first support rod with one second support rod. In another embodiment, the upper protecting frame 103 comprises four first support rods, with the spacing in-between the first support rods being the same or different; the lower protecting frame comprises four corresponding second support rods, with the spacing in-between the second support rods being the same or different. The four lifting mechanisms 302 are respectively disposed each at the intersection of one first support rod with one second support rod. In another embodiment, the number of the first support rods, of the second support rod, and of the lifting mechanism 302 is not prescribed, the number may be two, three, four, five, six, and so on.

In one embodiment, the lifting mechanism 302 is an electric lifting rod. The electric lifting rod is compact, does not take up extra space, and is easy to operate. In one embodiment, the number of electric lifting rods may be four. The number of electric lifting rods may be determined according to requisites of the surgeon doctor and the milieu.

In one embodiment, the medical radiation protection device 100 further comprises the opening and closing system. Referring to FIG. 1, FIG. 5 and FIG. 6, the opening and closing system comprises the rotating rod 105, the opening and closing motor and the opening and closing control device 107. The rotating rod 105 is disposed in the vertical direction of the barrel-shaped protecting frame 101. At least a portion of the barrel-shaped protecting frame 101 may rotate around the rotating rod 105 to open and close the protecting cover 102. The surgeon doctor enters the protecting cover 102 by means of opening the protecting cover 102; by closing the protecting cover 102, X-ray protection is initiated. The opening and closing motor is disposed on the rotating rod 105, and at least a portion of the barrel-shaped protecting frame 101 is opened or closed under action of the opening and closing motor to realize opening and closing of the protecting cover 102. The opening and closing control device 107 may be disposed at any position of the medical radiation protection device 100. For example, the opening and closing control device 107 may be disposed on the upper protecting frame 103 or the lower protecting frame 104 to facilitate user operation.

In one embodiment, the opening and closing control device 107 comprises two separate magnetic switch buttons. The two magnetic switch buttons are disposed on the upper protecting frame console 201 on the top of the upper protecting frame 103. The two buttons are marked with "On" and "Off" respectively to prevent wrong touching.

In one embodiment, the barrel-shaped protecting frame 101 is comprised of two semi-ring protecting shelves (having a semi-ring cross section) 109, 110, each end of which is connected via a rotating rod 105. The two semi-ring protecting shelves 109, 110 may rotate around the rotating rod 105 to close or open the barrel-shaped protecting frame 101, thereby opening or closing the protecting cover 102.

In one embodiment, referring to FIG. 1-4, on the bottom of the lower protecting frame 104 is provided with a moving caster 108. In another embodiment, the moving caster 108 is the universal caster. The universal caster may be rotated 360 degrees horizontally to facilitate steering of the medical radiation protection device 100, thereby facilitating maneuvering of the surgeon doctor during surgical operation, without hindering manual operation thereof, thus making the operation easier and more convenient.

Employment of the medical radiation protection device 100 is as follows: the surgeon doctor presses the "On" button on the barrel-shaped protecting frame 101, opening an entrance of the barrel-shaped protecting frame 101 by means of simultaneous manipulation of the rotating rod 105 and the opening and closing motor. The surgeon doctor then enters the barrel-shaped protecting frame 101 via the entrance and press the "Off" button of the opening and closing control device 107 to close the entrance. The protecting cover 102 serves as a side wall of the barrel-shaped protecting frame 101 and encircles the surgeon doctor in 360 degrees. The height of the barrel-shaped protecting frame 101 is adjustable by means of pressing the "Up" and "Down" buttons of the lifting control device 106.

Figure 7:
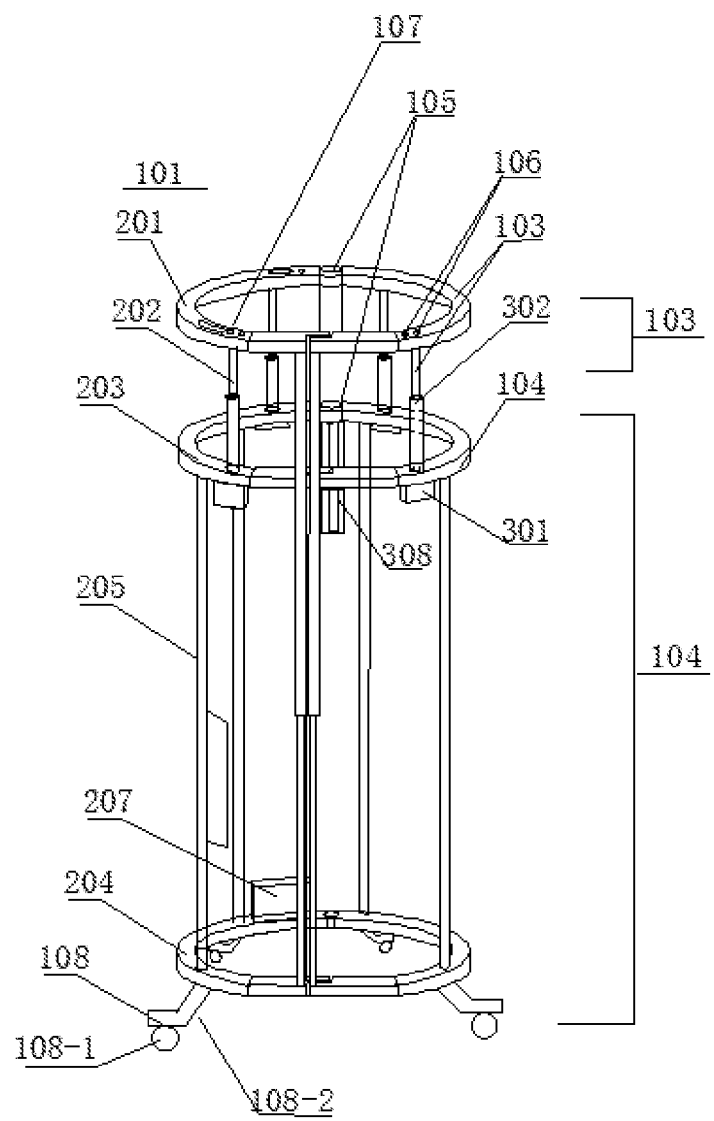
FIG. 7 is a schematic perspective view of the medical radiation protection device.

In another embodiment, referring to FIG. 7, the medical radiation protection device 100 comprises a barrel-shaped protection device 701. The barrel-shaped protection device 701 comprises an upper protection device 703 and a lower protection device 704. The inner diameter of the upper protection device 703 may be slightly larger or smaller than the inner diameter of the lower protection device 704. The upper protection device 703 and the lower protection device 704 are mutually connected, with the upper protection device 703 being movable along the outer or the inner sidewall of the lower protection device 704. The barrel-shaped protection device 701 is made of stainless steel and may also be made of metal alloys thereof. An X-ray protective material layer 702, such as a lead layer, is attached to a sidewall of the barrel-shaped protection device 701. The X-ray protective material layer 702 may be attached to any side of the inner sidewall, of the outer sidewall, and/or imbued within any of the side walls of the barrel-shaped protection device 701. In another embodiment, the medical radiation protection device 100 may further comprise the lifting system and the opening and closing system. The barrel-shaped protecting frame 101 is similar to the barrel-shaped protection device 701 except that the barrel-shaped protecting frame 101 is a support frame of the medical radiation protection device 100, and has no side walls, with the protecting cover 102 being connected to the barrel-shaped protecting frame 101 to serve as a side wall of the barrel-shaped protecting frame 101; while the barrel-shaped protection device 701 has a side wall, with the X-ray protective material layer 702 being disposed on any side of the inner sidewall, of the outer sidewall, and/or imbued within any of the side walls of the barrel-shaped protection device 701.

With adoption of the medical radiation protection device 100 according to various embodiments of the present disclosure, the surgeon doctor has no need to wear heavy lead clothing, thereby reducing the load thereof while further improving protective effect.

Figure 8:
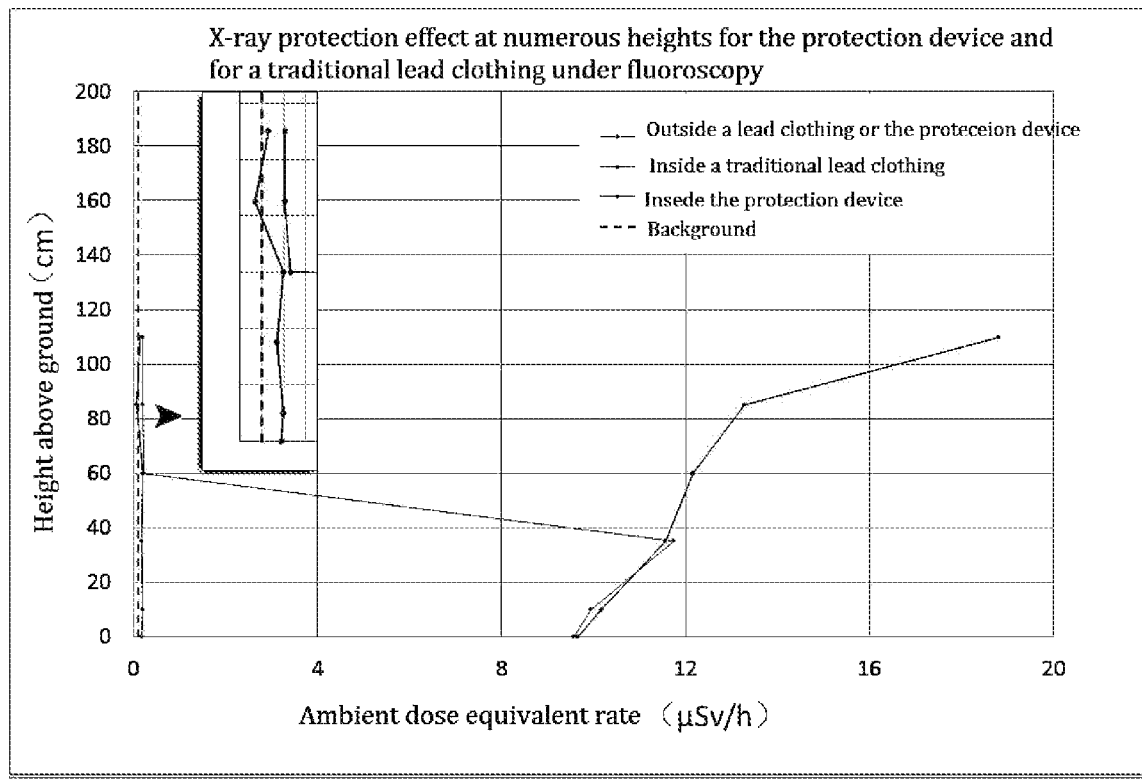
FIG. 8 is a schematic diagram comparing detection and analysis of the medical radiation protection device according to an embodiment of the present disclosure against a conventional lead clothing in an X-ray fluoroscopy state.
Figure 9:
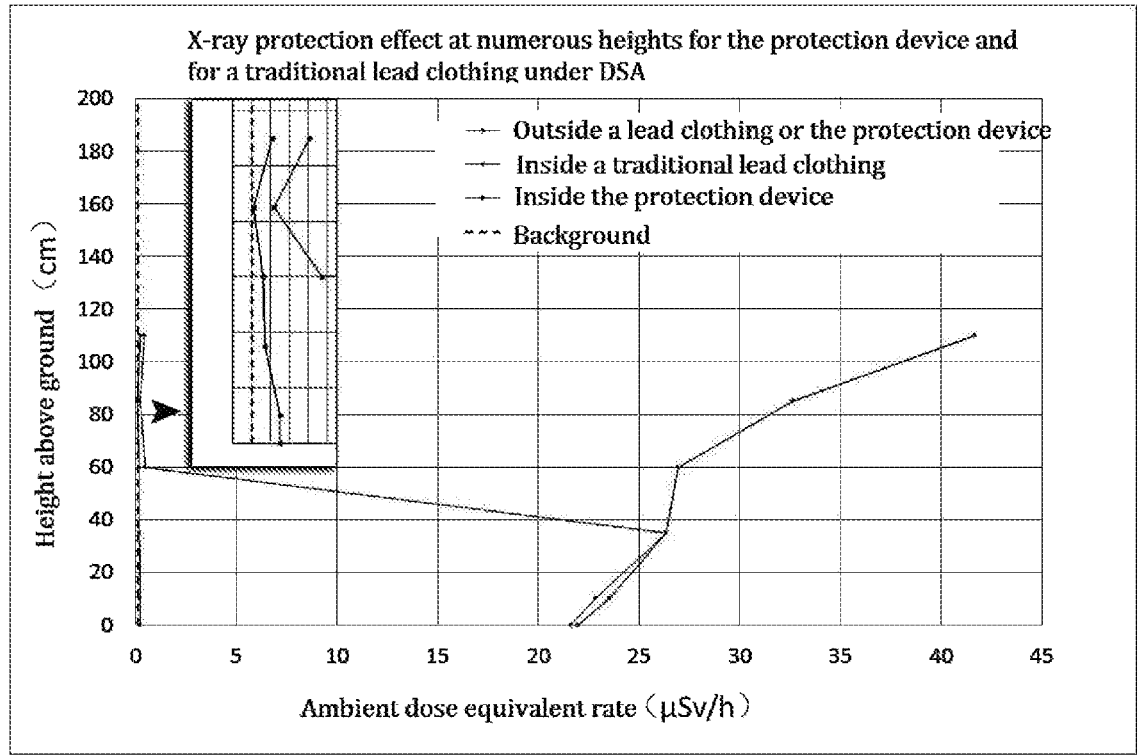
FIG. 9 is a schematic diagram comparing detection and analysis of the medical radiation protection device according to an embodiment of the present disclosure against a conventional lead garment in a DSA state.

Table 1, Table 2, FIG. 8 and FIG. 9 show radiation data for the medical radiation protection device 100 of the present disclosure in contrast to conventional lead clothing.

TABLE 1

| | Radiation data employing the medical radiation protection device | | | |
|---|---|---|---|---|
| | Ambient dose equivalent rate in fluoroscopy state (unit: µSv/h) | | Ambient dose equivalent rate in DSA state (unit: µSv/h) | |
| Position | Outside the device | Inside the device | Outside the device | Inside the device |
| Protection device level 6 (110 cm above ground) | 18.8 ± 0 | 0.13 ± 0.02 | 41.67 ± 4.16 | 0.21 ± 0.02 |
| Protection device level 5 (85 cm above ground) | 13.27 ± 0.06 | 0.07 ± 0.02 | 32.67 ± 0.58 | 0.11 ± 0.02 |
| Protection device level 4 (60 cm above ground) | 12.17 ± 0.23 | 0.2 ± 0.05 | 26.93 ± 0.57 | 0.16 ± 0.01 |
| Protection device level 3 (35 cm above ground) | 11.57 ± 0.06 | 0.17 ± 0.01 | 26.33 ± 0.25 | 0.17 ± 0.02 |
| Protection device level 2 (10 cm above ground) | 10.17 ± 0.06 | 0.2 ± 0.02 | 23.53 ± 0.35 | 0.25 ± 0.04 |
| Protection device level 1 (0 cm above ground) | 9.67 ± 0.06 | 0.19 ± 0.02 | 21.97 ± 0.23 | 0.25 ± 0.03 |

TABLE 2

| | Radiation data employing traditional lead clothing | | | |
|---|---|---|---|---|
| | Ambient dose equivalent rate in fluoroscopy state (unit: μSv/h) | | Ambient dose equivalent rate in DSA state (unit: μSv/h) | |
| Position | Outside the lead clothing | Inside the lead clothing | Outside the lead clothing | Inside the lead clothing |
| Protection device level 6 (110 cm above ground) | 12.8 ± 0.1 | 0.21 ± 0.01 | 28.53 ± 0.35 | 0.41 ± 0.07 |
| Protection device level 5 (85 cm above ground) | 8.27 ± 0.67 | 0.21 ± 0.02 | 19.9 ± 0.44 | 0.22 ± 0.08 |
| Protection device level 4 (60 cm above ground) | 12.17 ± 0.23 | 0.23 ± 0.05 | 26.93 ± 0.57 | 0.47 ± 0.12 |
| Protection device level 3 (35 cm above ground) | 11.73 ± 0.23 | | 26.37 ± 0.55 | |
| Protection device level 2 (10 cm above ground) | 9.93 ± 0.21 | | 22.87 ± 0.5 | |
| Protection device level 1 (0 cm above ground) | 9.57 ± 0.12 | | 21.6 ± 0.1 | |

Note:
positions which are below 35 cm above ground are not covered by the lead clothing.

It can be seen from the analysis data that positions below the knees of the surgeon doctor is "unprotected", be it for X-ray fluoroscopy or digital subtraction angiography (DSA) examination, due to the fact that traditional lead clothing does not reach below the knees (about 35 cm above ground). If the knees are covered, free movement of the surgeon doctor wearing traditional lead clothing would be hampered.

At a distance of 35 cm from above ground outside the medical radiation protection device 100, the highest ambient dose equivalent rate for fluoroscopy examination is 11.57±0.06 μSv/h, and the highest ambient dose equivalent rate for DSA is 26.33±0.25 μS/h. The dose equivalent rate around each height (height from above ground) in the device for employment of the medical radiation protection device 100 is lower than that around a same height in the case of employment of traditional lead clothing protection, be it for fluoroscopy or DSA. It can be seen that protective effect of the medical radiation protection device 100 disclosed in the present disclosure is superior to that of conventional lead clothing.

Outside the medical radiation protection device 100, an ambient dose rises rapidly in both fluoroscopy and DSA state (e.g., more than 40 μSv/h at 110 cm from above ground in a DSA state). The higher the height, the higher the ambient dose equivalent rate. The medical radiation protection device 100 disclosed herein can control most of the ambient dose equivalent rate to about a background radiation value (also referred to as background radiation), that is, the radiation value in the air. Most of the ambient dose equivalent rates are controlled below 0.2 μSv/h.

The medical radiation protection device 100 disclosed by the disclosure can effectively protect lower limbs at height of 35 cm or less from above ground, and has the same protective effect as at the height of 35 cm above ground, significantly superior to traditional lead clothing protection.

Figure 10:
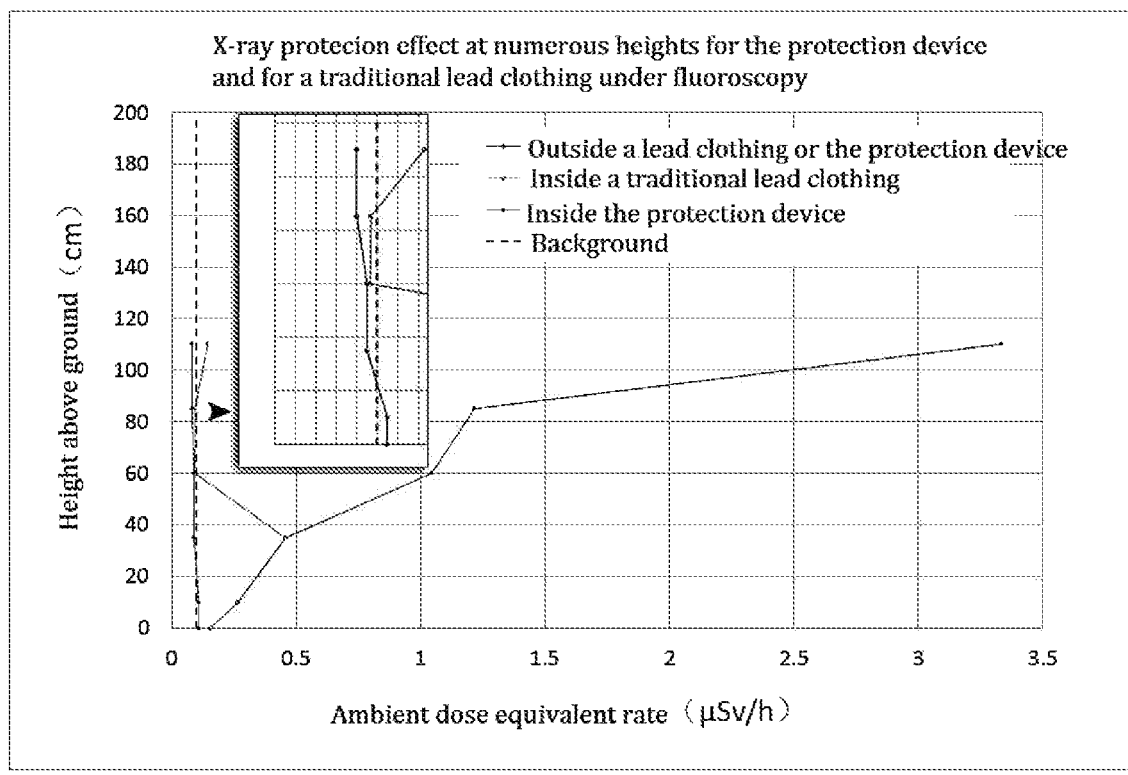
FIG. 10 is a schematic diagram comparing detection and analysis of the medical radiation protection device of another embodiment of the present disclosure with a lead baffle against a conventional lead garment in an X-ray fluoroscopy state.
Figure 11:
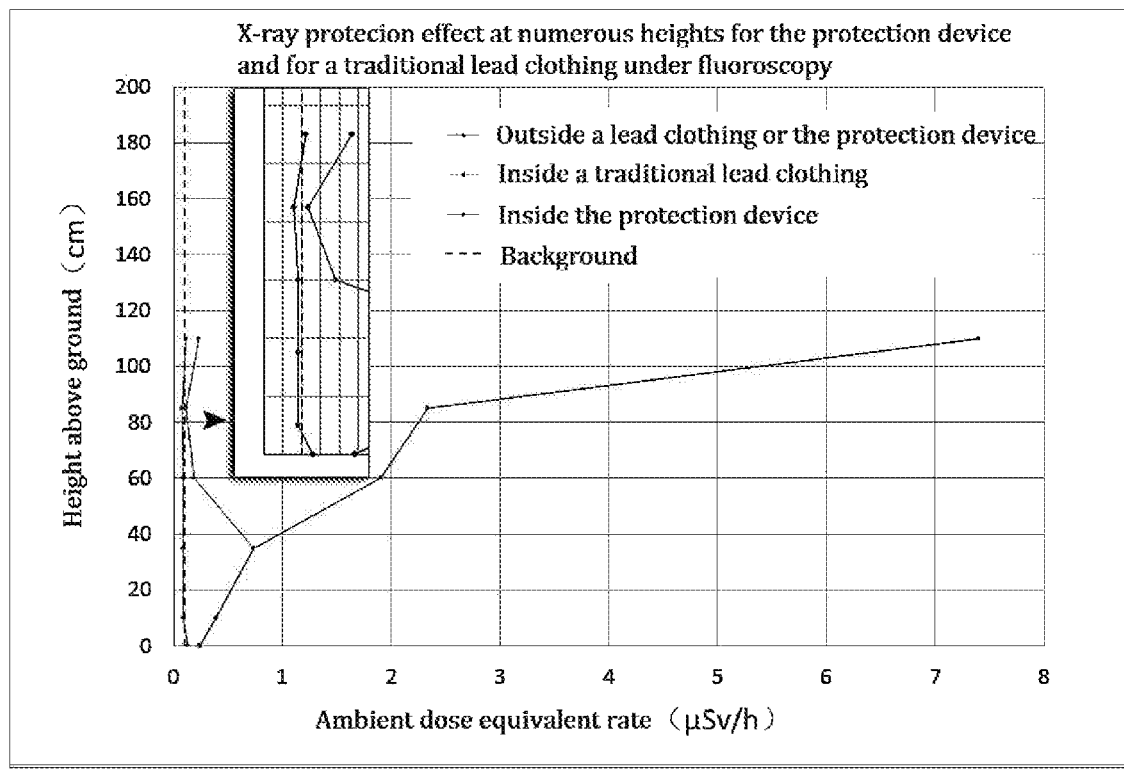
FIG. 11 is a schematic diagram comparing detection and analysis of the medical radiation protection device of another embodiment of the present disclosure with a lead baffle against a conventional lead garment in a DSA state.

Table 3, Table 4, FIG. 10 and FIG. 11 show radiation data for the protection device (1.0 lead equivalent) in contrast to conventional lead clothing (0.5 lead equivalent) with addition of a lead baffle.

TABLE 3

| | Radiation data employing the medical radiation protection devices (1.0 lead equivalent) | | | |
|---|---|---|---|---|
| | Ambient dose equivalent rate in a fluoroscopy state (unit: μSv/h) | | Ambient dose equivalent rate in a DSA state (unit: μSv/h) | |
| Position | Outside the device | Inside the device | Outside the device | Inside the device |
| Protection device level 6 (110 cm above ground) | 3.33 ± 0.31 | 0.08 ± 0 | 7.4 ± 0.35 | 0.11 ± 0 |
| Protection device level 5 (85 cm above ground) | 1.22 ± 0.08 | 0.08 ± 0 | 2.34 ± 0.06 | 0.08 ± 0 |
| Protection device level 4 (60 cm above ground) | 1.04 ± 0.06 | 0.09 ± 0 | 1.91 ± 0.03 | 0.09 ± 0 |
| Protection device level 3 (35 cm above ground) | 0.46 ± 0.17 | 0.09 ± 0 | 0.74 ± 0.03 | 0.09 ± 0 |

TABLE 3-continued

Radiation data employing the medical radiation protection devices (1.0 lead equivalent)

| Position | Ambient dose equivalent rate in a fluoroscopy state (unit: μSv/h) | | Ambient dose equivalent rate in a DSA state (unit: μSv/h) | |
|---|---|---|---|---|
| | Outside the device | Inside the device | Outside the device | Inside the device |
| Protection device level 2 (10 cm above ground) | 0.26 ± 0.03 | 0.11 ± 0.01 | 0.39 ± 0.05 | 0.09 ± 0 |
| Protection device level 1 (0 cm above ground) | 0.15 ± 0.01 | 0.11 ± 0.01 | 0.24 ± 0.05 | 0.13 ± 0.02 |

TABLE 4

Radiation data employing conventional lead clothing (0.5 lead equivalent)

| Position | Ambient dose equivalent rate in a fluoroscopy state (unit: μSv/h) | | Ambient dose equivalent rate in a DSA state (unit: μSv/h) | |
|---|---|---|---|---|
| | Outside the lead clothing | Inside the lead clothing | Outside the lead clothing | Inside the lead clothing |
| Protection device level 6 (110 cm above ground) | 3.33 ± 0.31 | 0.21 ± 0.01 | 7.4 ± 0.35 | 0.23 ± 0.03 |
| Protection device level 5 (85 cm above ground) | 1.22 ± 0.08 | 0.21 ± 0.02 | 2.34 ± 0.06 | 0.12 ± 0.02 |
| Protection device level 4 (60 cm above ground) | 1.04 ± 0.06 | 0.23 ± 0.05 | 1.91 ± 0.03 | 0.19 ± 0.1 |
| Protection device level 3 (35 cm above ground) | 0.46 ± 0.17 | | 0.74 ± 0.03 | |
| Protection device level 2 (10 cm above ground) | 0.26 ± 0.03 | | 0.39 ± 0.05 | |
| Protection device level 1 (0 cm above ground) | 0.15 ± 0.01 | | 0.24 ± 0.05 | |

Note:
positions which are below 35 cm above ground were not covered by lead clothing.

Outside the medical radiation protection device 100, the ambient dose rises rapidly in both fluoroscopy and DSA state (e.g., more than 7 μSv/h at 110 cm above ground in a DSA state). The higher the height, the higher the ambient dose equivalent rate. The protection device 100 disclosed herein can control the ambient dose equivalent rate below the background radiation value (radiation value in the air) in majority of cases, that is, below 0.1 μSv/h.

It can be seen that the protection device 100 disclosed in the present disclosure may adopt lead material with larger thickness or other protective material to achieve better protective effect.

Numerous specific details are set forth in the above description in order to provide a thorough understanding of the present disclosure. The present disclosure shall not be limited by the few preferred embodiments in the aforementioned description of the present disclosure, as the present disclosure may be implemented in numerous other manners than those described herein. At the same time, a person skilled in the art is capable of making numerous alterations and modifications to the technical solution of the present disclosure or modifying it to be equivalent embodiments, without departing from the scope of the technical solution of the present disclosure by employing the methods and technical skills disclosed there-above. Any simple alteration, equivalent change, or modification of the aforementioned embodiments in accordance with the technical spirit of the present disclosure shall fall within the scope of protection of the technical solution of the present disclosure.

The invention claimed is:

1. A medical radiation protection device, comprising a barrel-shaped protecting frame and a protecting cover, wherein the barrel-shaped protecting frame comprises an upper protecting frame and a lower protecting frame;
   the medical radiation protection device further comprises a lifting system, the lifting system comprising a lifting motor, a lifting mechanism and a lifting control device;
   the upper protecting frame is connected to the lower protecting frame (104) via the lifting mechanism, the upper protecting frame is supported by the lower protecting frame to move up or down under action of the lifting mechanism;
   the protecting cover is arranged around an inner side wall and/or an outer side wall of the barrel-shaped protecting frame;

the lifting control device comprises a button switch, a voice control device or a gesture control device; the button switch, the voice control device or the gesture control device are installed on the upper protection frame.

2. The medical radiation protection device according to claim 1, wherein the upper protecting frame comprises an upper protecting frame console and at least a first support rod; the upper protecting frame console comprises an upper protecting frame console panel and an upper protecting frame console support frame, and the upper protecting frame console panel is fixed on the upper protecting frame console support frame via a screw;

the first support rod is fixedly connected to a lower bottom surface of the upper protecting frame console and to the lifting mechanism, and is under control of the lifting mechanism for up or down movement; the lower protecting frame comprises a middle protecting frame support, a bottom support and a second support rod, with the middle protecting frame support and the bottom support being fixedly connected via the second support rod;

the lifting mechanism and the lifting motor are fixed on the middle protecting frame support;

the upper protecting frame console, the middle protecting frame support and the bottom support have a same cross-sectional shape; the upper protecting frame console is provided with a door panel along a secant direction, and a front and a rear side each of the door panel is in planar shape; correspondingly, the middle protecting frame support and the bottom support each is respectively provided with a door panel along a respective secant direction, and a front and a rear side each of the door panel is in planar shape;

the medical radiation protection device further comprises a charging device, with the charging device comprising a charging interface, a rechargeable battery and a power transmission interface, and the charging device is mounted on the lower protecting frame; the lifting motor is electrically connected to the power transmission interface;

the medical radiation protection device further comprises a power switch and a power indicator device, the power switch and the power indicator device being mounted on the upper protecting frame console; the power switch and the power indicator device are electrically connected respectively to the power transmission interface.

3. The medical radiation protection device according to claim 2, wherein the barrel-shaped protecting frame comprises a left and a right semi-ring protecting shelf;

the upper protecting frame console, the middle protecting frame support and the bottom support are separately divided each into a left part and a right part, with a left part and a right part being symmetric and matching each other; the two semi-ring protecting shelves are comprised respectively of left and right parts of the upper protecting frame console, of the middle protecting frame support and of the bottom support, as well as comprised of the first support rod and the second support rod.

4. The medical radiation protection device according to claim 3, wherein the medical radiation protection device further comprises an opening and closing system, the opening and closing system comprises a rotating rod, an opening and closing motor and an opening and closing control device;

the rotating rod is disposed in a vertical direction of the barrel-shaped protecting frame, and the opening and closing motor is disposed on the rotating rod, and at least a portion of the barrel-shaped protecting frame is rotated around the rotating rod for opening and closing the protecting cover;

an anti-pinch device is also provided on a face for switching and closing of the two semi-ring protecting shelves;

an end each of the two semi-ring protecting shelves is connected to one another via the rotating rod, the two semi-ring protecting shelves are rotated around the rotating rod for closing and opening the barrel-shaped protecting frame and the protecting cover.

5. The medical radiation protection device according to claim 4, wherein the opening and closing control device comprises a magnetic switch, a voice control device or a gesture control device.

6. The medical radiation protection device according to claim 3, further comprises a door strip, the door strip comprising an upper door strip and a lower door strip; the upper door strip is fixedly mounted on the upper protecting frame, the lower door strip is fixedly mounted on the lower protecting frame, and the lower door strip is inserted into the upper door strip for sliding movement.

7. The medical radiation protection device according to claim 2, wherein 3-5 universal casters are disposed at a bottom of the bottom support; the universal caster comprises a universal wheel and a universal wheel support frame, with an end of the universal wheel support frame being connected to the universal wheel, and an other end being fixedly connected to the bottom of the bottom support; an angle between the universal wheel support frame and an outer side wall of the bottom support is greater than or equal to 90 degrees, with the universal wheel being extended exterior to an outer side of the lower protecting frame under support of the universal wheel support frame.

8. The medical radiation protection device according to claim 2, wherein the door panel comprises a left door panel and a right door panel, a right end surface of the left door panel has an L shape in a horizontal direction, and a left end surface of the corresponding right door panel has an inverted L shape in a horizontal direction; a right end of the left door panel is embedded and sealed in a left end of the right door panel, for blocking radiation from entering the medical radiation protection device via a junction of the left door panel with the right door panel.

9. The medical radiation protection device according to claim 2, wherein the number of the first support rods is 3-4, and the number of sets of the lifting system is correspondingly 3-4; the number of the second support rods is 3-4; the rechargeable battery is a lithium battery, a lead acid battery, or a nickel hydrogen battery;

the barrel-shaped protecting frame is made of stainless steel, iron, gold, silver, copper, aluminum, zinc or manganese, the protecting cover is made of lead, lead material, radiation-proof inorganic lead glass, radiation-proof organic lead glass or fiber reinforced plastic composite protective material, and the protecting cover comprises a layer of X-ray protective material.

10. The medical radiation protection device according to claim 1, wherein the protecting cover comprises an upper protecting frame cover and a lower protecting frame cover; the upper protecting frame cover surrounds the upper protecting frame in a full circle, and the lower protecting frame cover surrounds the lower protecting frame in a full circle, a lower portion of the lower protecting frame cover extends to a horizontal floor; an outer side of an upper portion of the lower protecting frame cover closely fits an inner side of the upper protecting frame cover, a sum of a height of the upper protecting frame cover and that of the lower protecting frame cover is greater than a height of the medical radiation protection device.

11. The medical radiation protection device according to claim 10, wherein the upper protecting frame cover has an inner protecting cover and an outer protecting cover, respectively fixedly connected to an inner side wall and an outer side wall of the upper protecting frame; the lower protecting frame cover has an inner protecting cover and an outer protecting cover, respectively fixedly connected to an inner side wall and an outer side wall of the lower protecting frame; a distance between the inner protecting cover and the outer protecting cover of the upper protecting frame cover is greater than a distance between the inner protecting cover and the outer protecting cover of the lower protecting frame cover, permitting insertion of the lower protecting frame cover into the upper protecting frame cover for sliding movement.

12. The medical radiation protection device according to claim 10, wherein an upper end of the outer protecting cover of the upper protecting frame cover is further fixedly connected to a hook side or a loop side of a hook and loop, with the corresponding loop side or the hook side of the hook and loop being sewn at a corresponding position on an upper portion of an outer side of the inner protecting cover of the upper protecting frame cover; a suspension collar is respectively sewn at an upper end of the inner protecting cover of the upper protecting frame cover and at a junction of the outer protecting cover with the hook and loop thereof;

an upper end of the outer protecting cover of the lower protecting frame cover is fixedly connected to a hook side or a loop side of a hook and loop, with the corresponding loop side or the hook side of the hook and loop being sewn at a corresponding position on an upper portion of an outer side of the inner protecting cover of the upper protecting frame cover; a suspension collar is respectively sewn at an upper end of the inner protecting cover of the lower protecting frame cover and at a junction of the outer protecting cover with the hook and loop thereof;

the medical radiation protection device further comprises a fixed strip and a column; the column has an inverted "L" shape, or an "arc" shape, or a "T" shape, the columns are disposed along both sides of an upper end surface of the upper protecting frame console support frame, with the fixed strip passing through the suspension collar of the upper protecting frame cover and is fixedly suspended in an inner side of the column;

the columns are also arranged along both sides of an upper end surface of the middle protecting frame support, with the fixed strip passing through the suspension collar of the lower protecting frame cover and is fixedly suspended in the inner side of the column.

13. The medical radiation protection device according to claim 10, wherein a bottom of the lower protecting frame cover is provided with a foot operation opening and a universal wheel support mounting hole; the foot operation opening is in a shape of an arch, a square, or a semicircle.

* * * * *